United States Patent [19]

Jacobs

[11] 4,160,601
[45] Jul. 10, 1979

[54] BIOCONTAMINATION AND PARTICULATE DETECTION SYSTEM

[76] Inventors: Robert A. Frosch, Administrator of the National Aeronautics and Space Administration, with respect to an invention of Jacqueline M. Jacobs, Pasadena, Calif.

[21] Appl. No.: 880,727

[22] Filed: Feb. 24, 1978

[51] Int. Cl.[2] .................... G01N 21/32; G01J 3/48
[52] U.S. Cl. ................................ 356/404; 356/237
[58] Field of Search ................ 356/74, 76, 77, 173, 356/175–177, 179, 195, 202, 203, 209, 210, 212, 237, 404

[56] References Cited

U.S. PATENT DOCUMENTS

| | | | |
|---|---|---|---|
| 2,550,648 | 4/1951 | Sweet | 356/203 |
| 2,582,073 | 1/1952 | Scudda | 356/203 |
| 2,982,169 | 5/1961 | Enright | 356/202 X |
| 3,339,451 | 9/1967 | Shaifer | 356/209 |
| 3,449,053 | 6/1969 | Cannady et al. | 356/203 X |
| 3,702,734 | 11/1972 | Lindahl et al. | 356/38 |

FOREIGN PATENT DOCUMENTS 1243422  6/1961  Fed. Rep. of Germany.

OTHER PUBLICATIONS

*IBM Technical Disclosure Bulletin,* vol. 16, No. 1, Jun. 1973, "Surface Contamination Particle Counter", p. 212, (Hopkins et al.).

*IBM Technical Disclosure Bulletin,* vol. 12, No. 2, Jul. 1969, "Scanning Registration Densitometer", pp. 276–277, (Abramson).

*The Review of Scientific Instruments,* vol. 36, No. 1, Jan. 1965, "Scanning Microscope Densitometer," pp. 31–33, (Hartman).

*Primary Examiner*—F. L. Evans
*Attorney, Agent, or Firm*—Wilfred Grifka; John R. Manning; Monte F. Mott

[57] ABSTRACT

A method for determining the characteristics and amount of microscopic contaminants lodged on a photographed surface. An image enhanced full-color photographic negative and print are taken of the contaminated surface. Three black-and-white prints are developed subsequently from red, green and blue separation filter overlays of the color negative. Both the color and three monochromatic prints are then scanned to extract in digital form a profile of any contaminant possibly existing on the surface. The resulting profiles are electronically analyzed and compared with data already stored relating to known contaminants.

7 Claims, 2 Drawing Figures

BIOCONTAMINATION AND PARTICULATE DETECTION SYSTEM

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

This invention relates to a method for identifying an unknown microscopic contaminant by matching its spectral characteristics with a stored data bank containing profiles of known contaminants.

At the present time, no suitable method exists for ascertaining the characteristics of and identifying unknown microscopic particulates and microorganisms contaminating a particular surface without physically contacting that surface. While operational technology has already been used for evaluating macroscopic systems such as marine life, agriculture, and forestry, no similar satisfactory technology has been developed to study microscopic systems. The need for such an invention is obvious in any environment where sterility becomes a factor to be taken into account. For example, it is sometimes necessary that spacecraft leaving the bounds of earth be free of contamination. And, of course, the contamination problems faced by hospitals are ubiquitous. Related problems arise in surmounting environmental pollution caused by industrial effluent particulates, pesticides and many other microscopic pollutants.

SUMMARY OF THE INVENTION

The present invention is directed towards a method which has at its object the accurate identification and characterization of microorganisms or bacteria in the range of one to ten microns in size. It is another object of the present invention for the relationships and interactions existing between the various microorganisms and other biocontaminants to be studied. It is a further object of the present invention for the viability of microorganisms such as micrococcus to be determined. The invention utilizes a system of easily modified and commercially available equipment, thereby providing an efficient yet economical environment in which to practice the invention.

The invention entails photographing a particular surface assumed to be contaminated by an unknown type of microorganism or particulate. A color negative illustrating an enlarged view of the specimen is first produced. Individual color separation negatives are created by overlaying colored filters upon the original color negative and then photographing the overlaid negative. Both the original color negative and the color separation negatives then undergo image preprocessing to extract and clarify all possible information from their features. A color print is then developed from the clarified color negative. At the same time, individual black-and-white prints are developed from each color separation negative. All of the prints are then scanned electronically to ascertain their optical densities. Analog plots are generated to measure reflectance against wavelength. The analog plots are subsequently converted into digital form. The digital information relating to the unknown contamination is then compared to previously-stored information gathered about known types of contamination. By making an analysis of color separation in such a manner, an additional dimension thus can be utilized in successfully processing information relating to the unknown contaminants.

The novel features of the invention are set forth with particularity in the appended claims. The invention will best be understood from the following description when read in conjunction with the accompanying drawings.

DESCRIPTION OF THE PREFERRED EMBODIMENT

Figure 1:
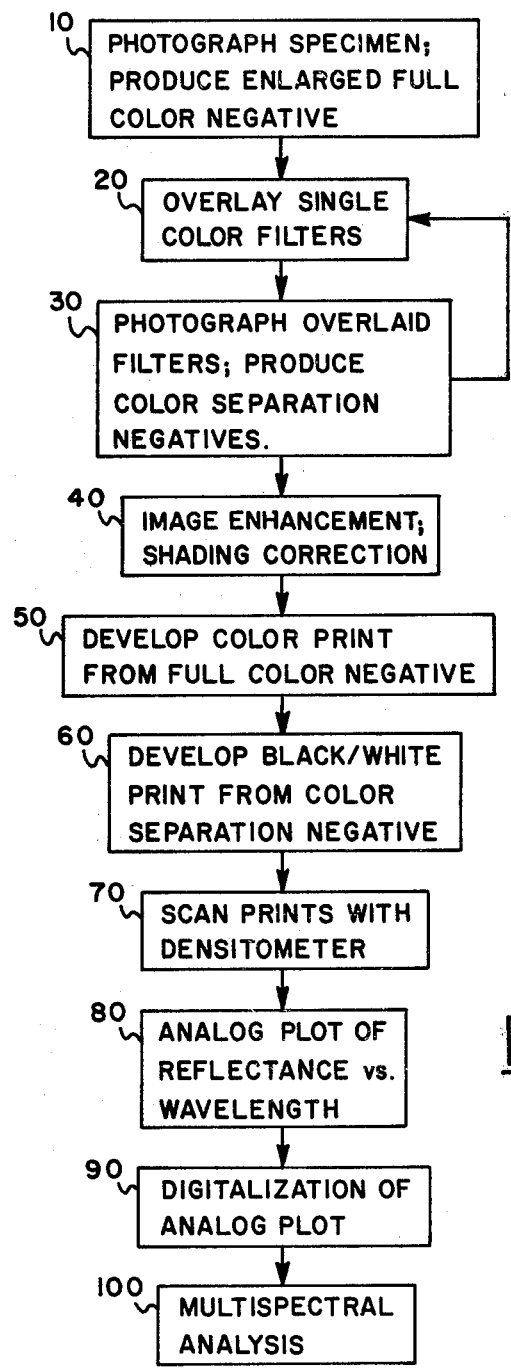
FIG. 1 is a schematic block diagram illustrating the method steps of the invention.

Attention is now directed to FIG. 1 wherein the first step 10 entails photographing a target surface as a specimen. An assumption is made that the specimen surface is possibly contaminated by some unknown variety or varieties of microscopic contaminants ranging in size between one to ten microns. Examples of such contaminants are particulates, bacteria, or microorganisms. In the preferred embodiment, the specimen will be placed at the bottom of a light box and photographed therein providing uniform shadowless lighting on the sample. A camera is employed which is capable of producing an enlarged full color negative of the specimen. It has been found that a suitable enlargement will be on the order of five times the size of the original. The enlargement must appear sharp and all important detail should be well-defined. The full-color negative functions as a baseline for identifying the spectral signature of the photographed unknown contaminants. Step 20 encompasses the utilization of color filters, each of which is composed of but a single color. In the preferred embodiment, only red, green and blue filters need be required. These three colors are chosen for their wide range over the chromatic spectrum. Each colored filter is overlaid one at a time either upon the full color negative or in front of the camera lens. Step 30 relates the photographing of the enlarged full color negative while covered over by each colored filter. This results in the production of a single color separation negative corresponding to each colored filter.

The four negatives (the original full-color negative and the three red, green, and blue color separation negatives) each undergo image preprocessing in step 40. The image enhancement techniques in this step are required to accentuate and clarify features in the negatives, thereby extracting all possible information from them. In the preferred embodiment, a conventional and commercially-available image-enhancement computer program may be used in successfully carrying out this step. The four negatives may also require at this time shading corrections to be made with the use of an input scanner unit. The shading gradients across a film frame, which are caused by unavoidable nonuniformities in specimen illumination and vignetting, can be effectively removed by applying a transformation derived from the digitized image of a flat field frame. In addition to shading corrections, the image preprocessing also involves means for multiband frame registration to be conducted. In the preferred embodiment, common registration between a set of color separation frames is accomplished by maximizing the cross correlation between translated reticle mark areas of consecutive pairs of images. This process ensures a registration accuracy to within plus or minus one pixel in translation. At the same time, rotation error is negligible, thereby requiring no computer correction. In contrast, normalization of image gamma is accomplished by applying a nonlinear contrast stretch based on the mean pixel values obtained from the graduated gray scale steps in the image. This final transformation yields a linear relationship between image pixel values and the known reflectance densities of the gray scale. By this process, the inevitable variations in film exposure, development and scanning which occur from specimen to specimen are normalized.

After step 40 is accomplished, a full color print then is developed from the original full-color negative in step 50. In a similar fashion step 60 sees the development of a black-and-white print from each of the specific color separation negatives. The resulting photographic images of the four prints are subsequently scanned with an electron beam in step 70. The scanning is typically performed with an automatic integrating densitometer, which is a standard instrument or photometer employed in measuring optical density. By definition, the optical density of a film or other material refers to the common logarithm of the opacity of that particular film. For example, film transmitting one hundred percent of light processes an optical density of zero, while a film transmitting ten percent has a density of one. As the densitometer scans the print, the exact position and intensity of the image may be related and possibly stored on magnetic tape. The scanning conducted in step 70 generates in step 80 analog plots measuring the percentage of incident light being reflected as a function of the optical wavelength. The various analog plots are converted by an appropriate conventional analog-to-digital device into digital form. The digitization process comprises step 90, the results of which can be recorded on a magnetic tape. In the final step 100, the digital information that has been thus generated from the unknown contaminants is analyzed and compared with data previously compiled relating to the characteristics or spectral signatures of known contaminants. This recorded information can be maintained by the establishment of a data bank electronically stored in a commercially-available digital computer, such as a conventional PDP 11/35 minicomputer. In essence, the procedure conducted in step 100 comprises a multispectral analysis in which diagnostics and histograms over the spectral waveband are used to match the spectral signatures or profiles of the known and unknown particulates and biocontaminants. By scanning the black-and-white negatives derived from the color separation negatives, a comparison with the baseline full-color print creates an additional dimension in which to more accurately identify the contaminants. In the preferred embodiment, the analysis is carried out with the aid of the commercially-available Image 100 system manufactured by the General Electric Company.

In addition to the precise identification of the unknown contaminants in step 100, the invention possesses the functional capability of determining the census of the contaminants resting upon the photographed surface. This added feature may be carried out, with a designated degree of precision, by suitable and appropriate mathematical tehniques. In the preferred embodiments, a portion of the output of the invention may be displayed suitably on a standard graphics display terminal wherein pseudo-colors are assigned to the various features of the surface, e.g., the shadows, background and different contaminants. In that way, each species of contaminant may be isolated and distinguished.

Figure 2:
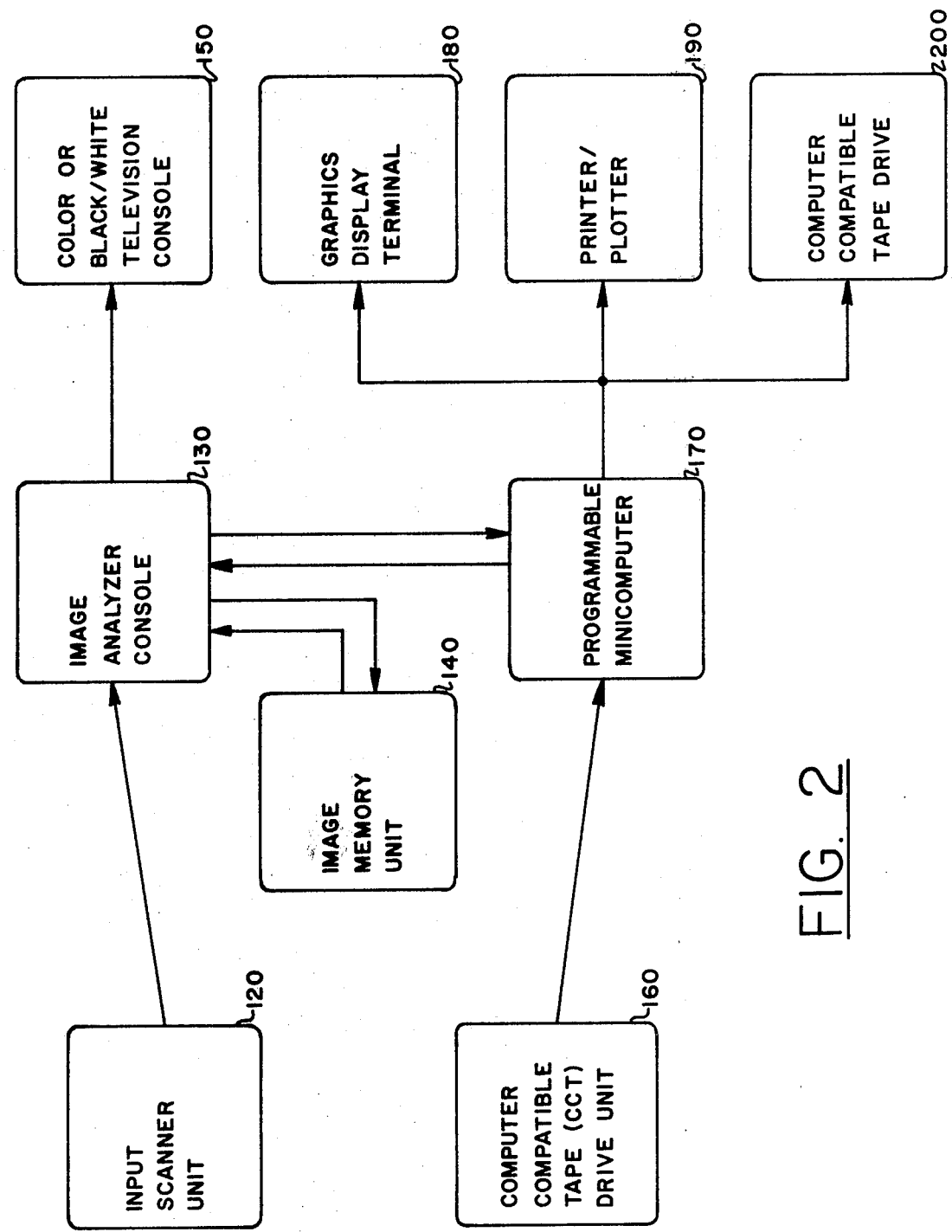
FIG. 2 is a block diagram illustrating the major pieces of image-processing equipment utilized in carrying out the invention.

Attention is now directed to FIG. 2 wherein the image processing functions of the present invention are depicted. A commercially-available input scanner unit 120 comprising an automatic densitometer device (not shown) provides the means for scanning an enlarged full-color photographic negative previously taken of a contaminated target specimen. In addition to the full-color negative, a series of individual single-color separation negatives also previously taken of the identical scene are scanned by unit 120. Both video averaging techniques and adjustments for shading corrections may be applied to the input scanner 120 to thereby insure proper correlation between the full-color and color separation negatives during the scanning process. Data derived from scanning unit 120 relates to a variety of such optical characteristics as the particular optical density or opacity of the film. The form of the data can be suitably digitized and recorded on magnetic tapes. This data then is transmitted electronically from input scanner unit 120 to an image analyzer console 130. Console 130 is wired electronically to an image memory unit 140 providing a data path in both directions between the two units. The digital data originating in scanner unit 120 therefore can be stored in memory unit 140 until such time as is required for processing its information. At the same time, information relating to previously compiled data gathered with respect to the characteristic or spectral signatures of known contaminants has been maintained in a data bank stored on a computer compatible tape drive unit 160. This data bank has the capability of split screen formatting and is of the type conventionally utilized in handling information derived from earth satellites. A programmable minicomputer 170, which is controlled by image analyzer console 130, conducts the actual multispectral analysis and calculations required in attempting to identify the unknown contaminant.

The minicomputer, which in the preferred embodiment is the commercially-available Digital Electronics Company PDP 11/35, uses data base management techniques to compare the data stored in tape drive unit 160 with data stored in memory unit 140. Techniques employed by the programmable minicomputer 170 include standard diagnostics and image enhancement procedures. Measurements are conducted and histograms are generated and analyzed in the effort. Results obtained from the minicomputer 170 can be displayed in three forms. A conventional graphics display terminal 180 has the advantage of being able to represent not only histograms and alphanumeric text, but also whatever densitometer displays have been developed during the process. An alternative output device is a standard printer/plotter unit 190, which is suitable for recording statistical reports, theme maps and a user action log. Another possible terminal remains a computer compatible tape drive unit 200 for use outputting data stored on computer magnetic or digital video tape. Finally, a feasible unit for displaying results directly from the spectrum analysis procedures is a color or black-and-white television console unit 150 mounted to image analyzer console 130. Television console 150 can provide immediate visual data relating to contaminants on the target surface.

Although particular embodiments of the invention have been described and illustrated herein, it is recognized that modifications and variations may readily occur to those skilled in the art and, consequently, it is intended that the claims be interpreted to cover such modifications and equivalents.

What is claimed is:

1. A method of determining the characterisitics of an unknown microscopic contaminant existing on a surface, comprising the steps of photographing said surface to produce an enlarged full-color photographic negative, overlaying said full-color negative one at a time with a plurality of individually different single-color filters, and consecutively photographing the image produced by each overlaid filter on said full color negative to create an equal number of color separation negatives, image-enhancing said full-color negative and each of said color separation negatives to produce respectively a clarified image-enhanced full-color negative and a plurality of clarified image-enhanced color separation negatives, developing a color print from said image-enhanced full-color negative, developing a single monochromatic print from each of said image-enhanced color separation negatives, scanning said color print and each of said monochromatic prints separately to produce profiles of reflectance as a function of optical wavelength, and comparing said reflectance profiles of contaminants with previously stored profiles of known contaminants produced in the same way, said previously stored profiles describing a known spectral signature characteristic of a known contaminant, said comparing being accomplished by matching profiles of said unknown contaminants with said stored profiles, each matching profile thus identifying an unknown microscopic contaminant.

2. The method as defined by claim 1 further comprising the step of counting the number of identified contaminants upon the photographed surface for each species of contaminants.

3. The method as defined by claim 1, wherein said single-color filters number at least three.

4. The method as defined by claim 3, wherein said single-color filters comprise red, green and blue filters.

5. The method as defined by claim 1, wherein said step of photographing said surface produces a shadowless full-color negative, said shadowless negative being enlarged at least five times that of said surface.

6. The method as defined by claim 1, wherein said step of scanning a print for optical density is carried out with a densitometer.

7. A method of isolating and identifying an unknown microscopic contaminant existing on a surface, said unknown contaminant having an unknown spectral signature, said unknown signature being individually distinctive to said unknown contaminant, which comprises the following steps:

photographing said surface to produce an enlarged full-color photographic negative, said full-color negative serving as a baseline for identifying said unknown spectral signature, overlaying said full-color negative one at a time with a plurality of single-color filters, said filters each having individually different colors, said full-color negative and said overlaid filters being photographed consecutively to create an equal number of color separation negatives;

image-enhancing said full color negative and each of said color separation negatives to produce respectively a clarified image-enhanced full-color negative and a plurality of clarified image-enhanced color separation negatives;

developing a color print from said image-enhanced full-color negative;

developing a single monochromatic black-and-white print from each of said image-enhanced color separation negatives;

optical density scanning said color print and each of said monochromatic prints, said scanning generating a plurality of analog plots, said analog plots measuring a percentage of incident light reflectance with respect to an optical wavelength, said plots providing a spectral signature for said unknown microscopic contaminant;

converting each of said analog plots into a digital form, said digital forms being stored electronically; and comparing said digital forms to a plurality of profiles stored in a data bank, said profiles describing a known spectral signature characteristic of a known contaminant, said comparing being accomplished by matching said unknown spectral signature with said profiles, said matching identifying said unknown microscopic contaminant.

* * * * *